(12) United States Patent
Tsubouchi

(10) Patent No.: US 12,137,889 B2
(45) Date of Patent: Nov. 12, 2024

(54) EXPANSION DEVICE FOR OPENING VALVE PERIMETER IN CARDIAC SURGERY

(71) Applicant: TERUMO CARDIOVASCULAR SYSTEMS CORPORATION, Ann Arbor, MI (US)

(72) Inventor: Takeshi Tsubouchi, Dexter, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 457 days.

(21) Appl. No.: 17/503,493

(22) Filed: Oct. 18, 2021

(65) Prior Publication Data

US 2022/0031299 A1    Feb. 3, 2022

Related U.S. Application Data

(63) Continuation of application No. PCT/US2020/030912, filed on May 1, 2020.
(Continued)

(51) Int. Cl.
*A61B 17/02* (2006.01)
*A61B 34/00* (2016.01)
*A61B 17/00* (2006.01)

(52) U.S. Cl.
CPC ...... *A61B 17/0218* (2013.01); *A61B 17/0206* (2013.01); *A61B 34/71* (2016.02);
(Continued)

(58) Field of Classification Search
CPC ..... A61B 34/71; A61B 34/02; A61B 34/0206; A61B 34/0218
See application file for complete search history.

(56) References Cited

U.S. PATENT DOCUMENTS

| | | |
|---|---|---|
| 5,290,308 A | 3/1994 | Knight et al. |
| 2005/0096508 A1 | 5/2005 | Valentini et al. |

(Continued)

FOREIGN PATENT DOCUMENTS

| | | |
|---|---|---|
| JP | H06154160 A | 6/1994 |
| JP | 2009534158 A | 9/2009 |

(Continued)

OTHER PUBLICATIONS

TeDan Surgical Innovations, CT Ultravision™, Mitral Valve Exposure Systems, 2015.
(Continued)

*Primary Examiner* — Christopher J Beccia
(74) *Attorney, Agent, or Firm* — Fish & Richardson P.C.

(57) ABSTRACT

A tissue expander/retractor tool works within a narrow cavity/tunnel to access a deeper structure (e.g., the mitral valve) without consuming a significant amount of space either within the small through-hole or in the vicinity of the entrance to the port. The tool provides the user with direct control of the expansion and separation of a target area. The moving parts of the tool have a closed configuration with a narrow profile for insertion/removal and an open configuration obtained using a remotely-controlled, compact pivot mechanism that provides a broad enlargement capability for the retraction jaws. A pantograph mechanism with input pivots and output pivots is coupled between the retraction jaws and a compound cable (e.g., Bowden cable). A handle is coupled to the other end of the compound cable for displacing the inner wire along the outer tube.

14 Claims, 6 Drawing Sheets

Related U.S. Application Data

(60) Provisional application No. 62/841,320, filed on May 1, 2019.

(52) U.S. Cl.
CPC ............... *A61B 2017/00243* (2013.01); *A61B 2017/00946* (2013.01)

(56) References Cited

U.S. PATENT DOCUMENTS

| | | | |
|---|---|---|---|
| 2005/0228232 | A1 | 10/2005 | Gillinov et al. |
| 2006/0052671 | A1 | 3/2006 | McCarthy |
| 2008/0021285 | A1 | 1/2008 | Drzyzga et al. |
| 2011/0046448 | A1 * | 2/2011 | Paolitto .............. A61B 17/0206 |
| | | | 128/898 |

FOREIGN PATENT DOCUMENTS

| | | | | |
|---|---|---|---|---|
| WO | | 9817182 A1 | 4/1998 | |
| WO | WO-2007127199 | A1 * | 11/2007 | ......... A61B 1/00052 |

OTHER PUBLICATIONS

Japanese Official Action, Application No. 2021-564490, mailed Oct. 31, 2023.

\* cited by examiner

Closed

Opened

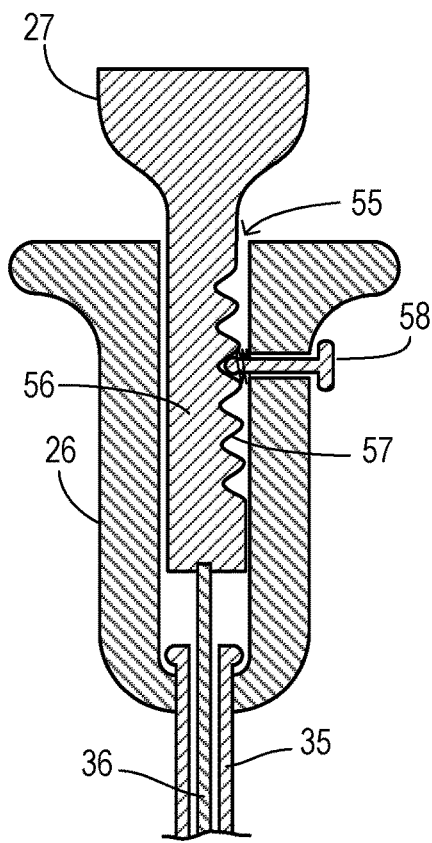
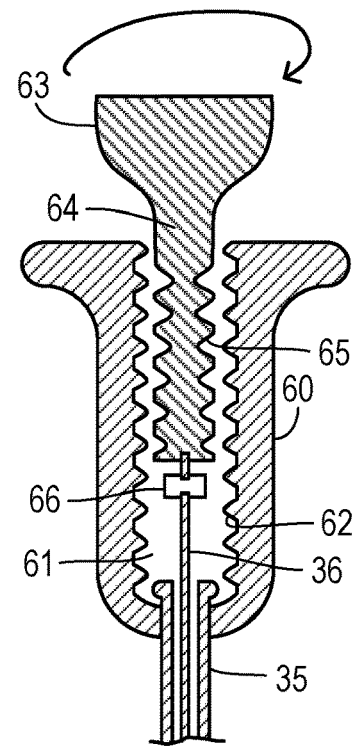
Fig. 8      Fig. 9
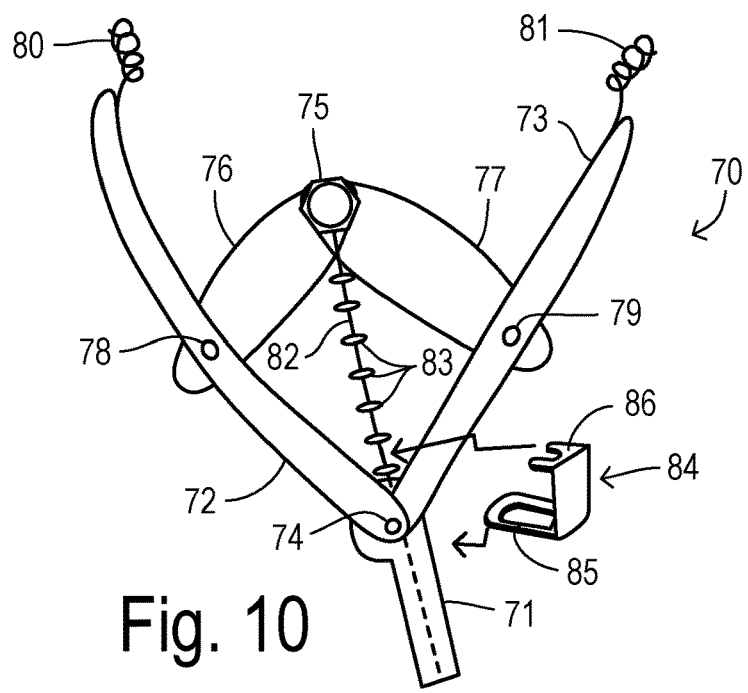
Fig. 10

EXPANSION DEVICE FOR OPENING VALVE PERIMETER IN CARDIAC SURGERY

CROSS REFERENCE TO RELATED APPLICATIONS

This application is a continuation of PCT Application serial number PCT/US20/30912, filed May 1, 2020, based on and claiming priority to U.S. Provisional Application Ser. No. 62/841,320, filed May 1, 2019, both of which are incorporated herein by reference.

BACKGROUND OF THE INVENTION

The present invention relates in general to a tool for minimally-invasive cardiac surgery, and, more specifically, to an expander insertable into cardiovascular structures for widening an opening or gap such as a perimeter around a cardiac valve for surgical repair.

The use of minimally-invasive cardiac surgery (MICS) has become a commonplace method for performing cardiac valve repair. MICS typically includes creating a working space within a chest space, such as the use of a lift winch type retractor for bypass grafting. In the case of mitral valve repair, a retractor blade may be pulled up by a shaft through an incised opening in the chest wall. In robotic or port surgeries, an airtight sealing port may be used for inserting various instruments while $CO_2$ gas in introduced to create an expanded cavity for the working space. Known devices may be less effective if the target area is deep inside of chest so that retraction from a single side is less effective for exposing the desired target areas (due to a tunnel or tight gap). The size of the entrance space (i.e., incision) for the MICS surgery is a very important factor since this dictates cosmetic outcomes of the MICS surgery.

Surgical tools must be manipulated through one or more small holes (i.e., ports). Any items inserted through a port may potentially interfere with or compete for space with other items entering the same port. Thus, minimizing the obstruction caused by an instrument or tool around the incision hole is an important objective.

SUMMARY OF THE INVENTION

This invention provides tools for surgical operations which enable a surgeon to spread open (i.e., expand) a tissue structure deep within an excised port (such as an incision in an atrial wall) by an adequate amount while working within a narrow cavity/tunnel to access a deeper structure (e.g., the tricuspid valve or the mitral valve) without consuming a significant amount of space either within the small throughhole or in the vicinity of the entrance to the port. The tool provides the user with direct control of the expansion and separation of a target area. The moving parts of the tool have a closed configuration with a narrow profile for insertion/removal and an open configuration obtained using a remotely-controlled, compact pivot mechanism that provides a broad enlargement capability for the retraction jaws.

In one aspect of the invention, an expander/retractor for minimally invasive cardiac surgery comprises a pantograph with input pivots and output pivots. First and second retraction jaws extend from the output pivots. A compound cable (i.e., Bowden cable) has an outer tube fixed to an input pivot and an inner wire fixed to another input pivot. A handle is coupled to the other end of the compound cable for displacing the inner wire along the outer tube. The retraction jaws have an adjustable shape (e.g., they may be comprised of a malleable wire for manually shaping them during use according to the needs of a particular situation or for reducing a profile of the jaws for more easily passing through an incised port into an inner working space).

The invention provides locational retraction and expansion for biological tissue and organs. Operation of the expander is accomplished using a thin cable (outer tube and inner wire) so that it does not occupy much space at the incision hole area.

BRIEF DESCRIPTION OF THE DRAWINGS

FIG. 8 is a cross-sectional view of a first embodiment of a handle for controlling the Bowden cable.

FIG. 9 is a cross-sectional view of a second embodiment of a handle for controlling the Bowden cable.

FIG. 10 is a side view of a pantograph/retractor jaw with a lock/latch mechanism.

DETAILED DESCRIPTION OF PREFERRED EMBODIMENTS

Figure 1:
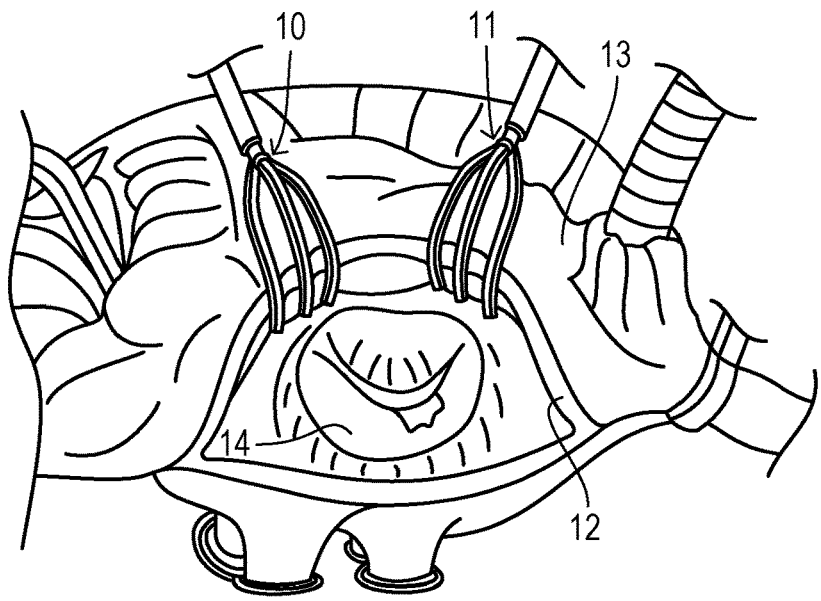
FIG. 1 depicts surgical access to a mitral valve via an incision port through a patient's chest and through an incision in an atrial wall.

Referring to FIG. 1, a mitral valve repair procedure wherein a pair of retractor rakes 10 and 11 are shown pulling open an incision 12 (e.g., an incision in an atrial wall 13) to expose a mitral valve 14. In MICS, a spoon or paddle may also be used as a retractor. Such rakes, spoons, and paddles are mounted on rigid rods which are anchored to a fixed frame secured outside the access port and which transmit the retraction forces by clamping the rods in a particular position on the frame. Consequently, significant space may be taken up in the access port and around its external periphery.

Figure 2:
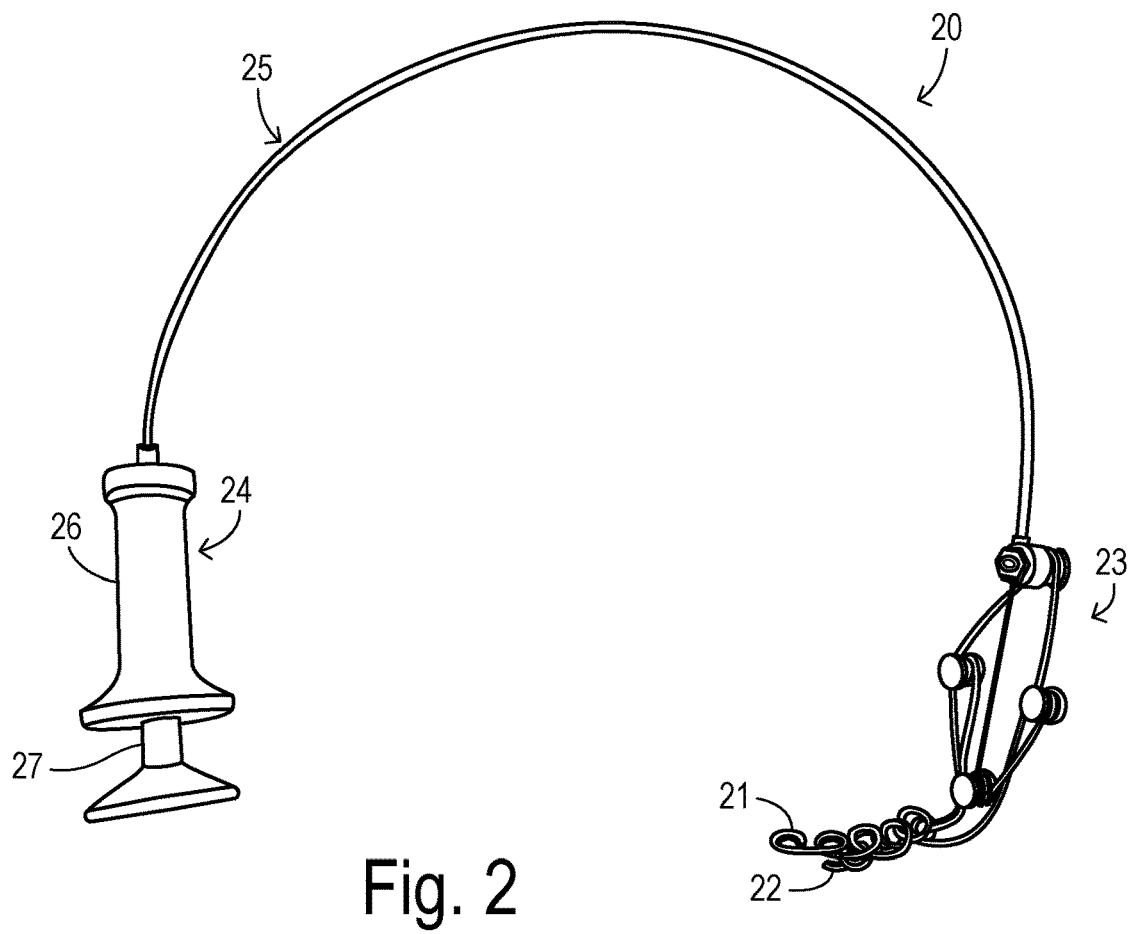
FIG. 2 is a side view of an expansion/retraction tool in a closed configuration.
Figure 3:
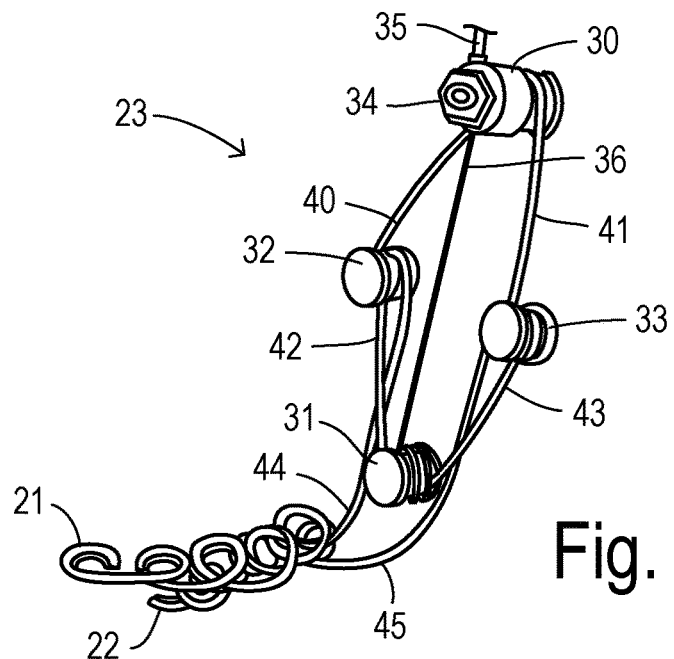
FIG. 3 is a side view showing the distal end of the tool of FIG. 2 in greater detail.

FIGS. 2 and 3 show a first embodiment of the invention for eliminating the rigid rods and the requirement for attaching to a fixed external frame while providing a wide retraction range achievable in a deep location within a cavity created in the body. An expander/retractor tool 20 includes retraction jaws 21 and 22 to push out tissue to create an opened space. Jaws 21 and 22 preferably are comprised of a malleable wire which can be bent by a surgeon to assume a desired shape while remaining sufficiently stable to retract the target tissue without further bending. The malleable wire may be wound in substantially coplanar loops for combining ease of re-shaping with a good lateral surface for bearing against the retracted tissue. Jaws 21 and 22 extend from a pantograph mechanism 23 (e.g., bar structures with hinges/pivots to convert push/pull force to a sideways retraction force). Pantograph mechanism 23 is similar to a "scissor jack" in which controlling a separation of two opposite corners of a parallelogram reciprocally controls separation of the other two opposite corners. Pantograph mechanism 23 is controlled by a handle 24 and a link cable 25 (e.g. a Bowden cable). Cable 25 is a compound cable having an outer tubing (i.e., jacket) and an inner wire to transfer a push/pull force through a thin structure. Handle 24 is a two-part handle with a body 26 and a plunger 27. The outer tubing of cable 25 is fixed to body 26, and inner wire of cable 25 is fixed to plunger 27. Body 26 is held by the user while reciprocating movement of plunger 27 converts natural hand motion to the wire push/pull motion.

Retraction jaws (fingers) 21 and 22 interface with the target organ or tissue to transfer push/retract forth to make space for performing surgery (e.g., valve leaflet repair or replacement). By adjusting pantograph mechanism 23, jaws 21 and 22 move laterally toward or away from each other. When jaws 21 and 22 are close together, pantograph mechanism is compressed so that the distal end of tool 20 has a narrow configuration for ease of insertion through the incised port and into the working space. As shown in greater detail in FIG. 3, pantograph mechanism 23 has input hinges 30 and 31 and output hinges 32 and 33. Linkages (i.e., link bars) 40 and 41 pivotally connect input hinge 30 to output hinges 32 and 33, respectively. Linkages 42 and 43 pivotally connect input hinge 31 to output hinges 32 and 33, respectively. An outer tube 35 of the Bowden cable is affixed to input hinge 30. An inner wire 36 of the Bowden cable slidably passes through input hinge 30 and is affixed to input hinge 31. Output arms 44 and 45 extend from output hinges 32 and 33 and have jaws 21 and 22 at their distal ends.

Longitudinal movement of wire 36 changes a distance between input hinges 31 and 32 (i.e., wire 36 is sufficiently unbending to push against input hinge 31, unless a biasing force is provided by any of the hinges against the linkages to urge pantograph mechanism 23 to a closed positon). Thus, pantograph mechanism 23 converts push/pull forces applied to the plunger and transmitted by the Bowden cable into a displacement of output hinges 32 and 33 which laterally retract jaws 21 and 22 (e.g., between opened and closed positions). Cable 25 and or handle 24 may include an embedded spring coil or other biasing element to provide either a normally opened or normally closed condition for jaws 21 and 22.

Linkages 40-43 can be comprised of the same partly malleable wire used to form jaws 21 and 22, for example. In that case, hinges 30-33 may be comprised of simple blocks around which the wires are wound (i.e., no moving parts are needed). The wires for output arms 44 and 45 can be a continuation of the wires for forming one or more of the other linkages.

Figure 4:
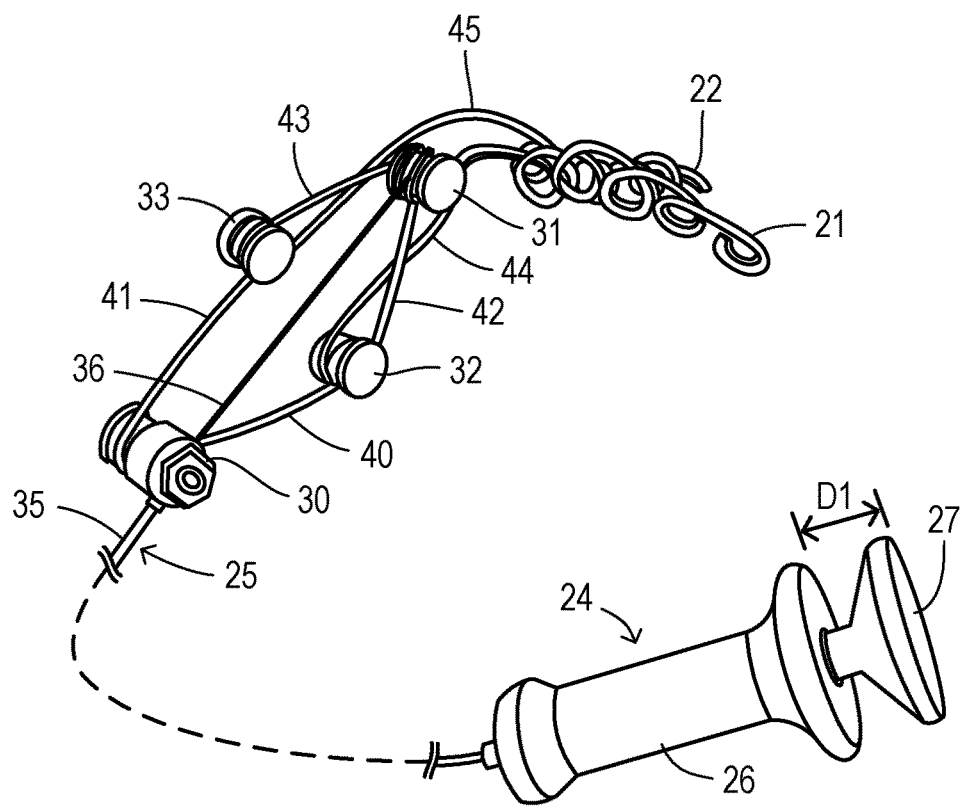
FIGS. 4 and 5 show the closed and opened configurations, respectively, according to pantograph movement controlled via the handle.
Figure 5:
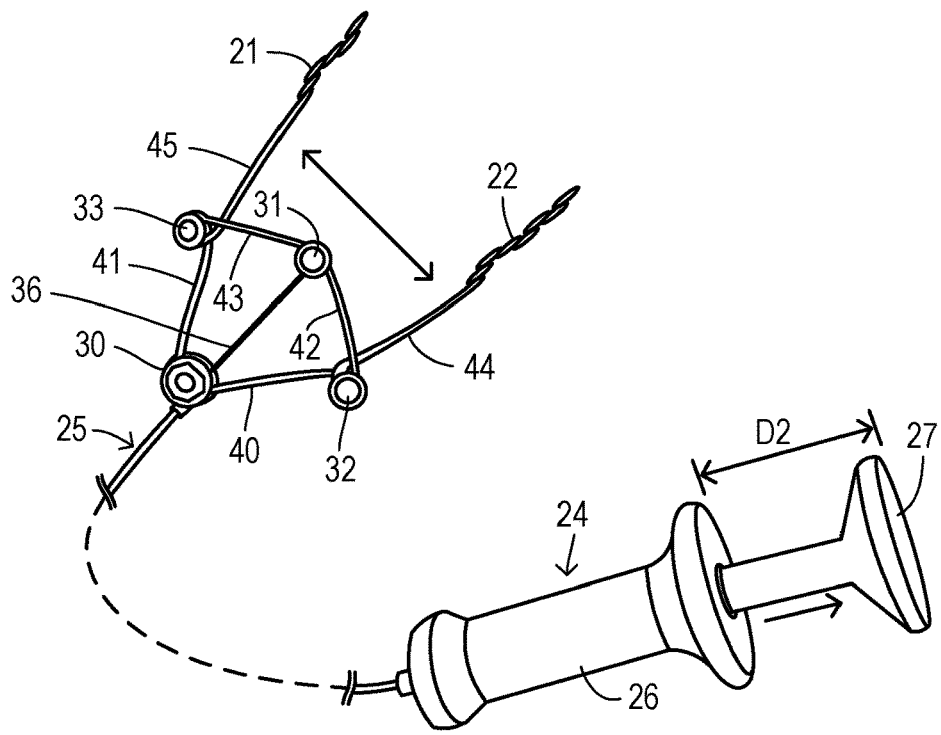

FIG. 4 shows a closed position of jaws 21 and 22 as a result of handle 24 having plunger 27 fully inserted to a distance D1. FIG. 5 shows an opened position of jaws 21 and 22 as a result of plunger 27 being withdrawn from body 26 by a distance D2 which causes input hinges 30 and 31 to approach each other by the same distance. Because of the actions of linkages 40-42, output hinges 32 and 33 move apart, carrying output arms and jaws 21 and 22 apart. Thus, push-pull forces are transferred from handle 24 to pantograph structure 23.

Figure 6:
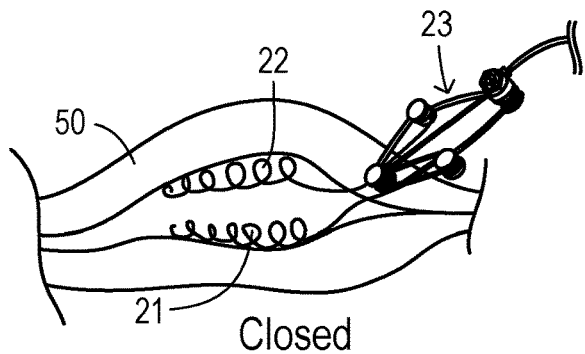
FIGS. 6 and 7 are diagrams depicting the closed and opened configurations, respectively, acting on a tissue structure to be retracted.
Figure 7:
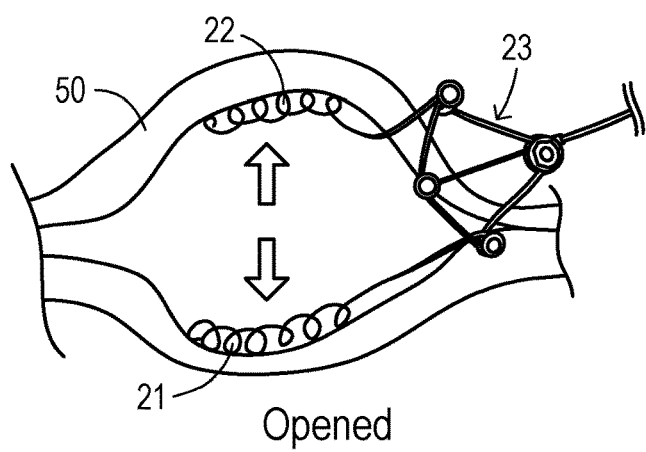

FIGS. 6 and 7 show the closed and opened states of the tool, respectively, when inserted into a tissue to be retracted. For example, the tool is inserted from a main incision hole to access an area to be retracted such as an atrial wall 50 which has been incised to access internal cardiac structures (e.g., a mitral valve, or a tricuspid valve). After placement within the structures to be retracted, retraction jaws 21 and 22 are deployed by pulling handle. Specifically, pulling the inner handle causes the inner wire to move towards the proximal end. This causes one end of pantograph mechanism 23 to move towards the opposite end. In response, the side hinges/pivots spread apart. The displacement between the retraction jaws is proportional to the displacement of the handle. The handle is held at the desired position to get good view and space of the target area.

In a preferred embodiment, the position of the handle can be locked with a handle locking mechanism. FIG. 8 shows a first embodiment wherein handle body 26 has an internal cavity 55 receiving a shaft 56 of plunger 27. Bowden wire 36 is affixed to an end of shaft 56. One side of shaft 56 has a series of grooves 57 for receiving a side lock pin 58. Pin 58 may have a biasing mechanism such as a spring (not shown) for urging pin 58 into a groove 57 to restrain movement of shaft 56 within body 26. FIG. 9 shows an alternative embodiment wherein a body 60 has an internal bore 61 with a threaded surface 62. A plunger 63 has a shaft 64 with a threaded outer surface 65 complementary to threaded surface 62. Bowden wire 36 is coupled to shaft 64 through a spinner 66 to avoid twisting of wire 36 when plunger 63 is rotated clockwise or counterclockwise to displace plunger 63 within body 60.

FIG. 10 shows another embodiment of a locking mechanism which may be placed at the pantograph mechanism. Thus, a distal end of a tool 70 includes a fixed hub 71 providing an input hinge connected to side arms 72 and 73 by a hinge pin 74. A second input hinge 75 is pivotally connected to drive arms 76 and 77. The other ends of arms 76 and 77 are pivotally connected to side arms 72 and 73 by hinge pins 78 and 79, respectively. Retractor fingers 80 and 81 extend from the distal ends of side arms 72 and 73, respectively. Hub 71 is fixed to the outer jacket of a Bowden cable, and an inner wire 82 of the Bowden cable is attached to input hinge 75. Wire 82 carries a series of spaced balls or beads 83. A C-shaped locking clip 84 has a mounting slot 85 which slidably receives hub 71 so that a pronged end 86 can be selectably clipped onto wire 82 between adjacent balls 83 to lock wire 82 to a particular position (i.e., preventing longitudinal movement of wire 82). With C-shaped clip 84, a handle positioning lock is no longer needed. Furthermore, with an ability to lock an opened position of fingers 80 and 81, the handle can be made to be removable. Consequently, the handle can be detached, leaving only the wire mechanism inside the chest cavity. This eliminates interference caused by the removable portion at or near the incision hole. The distal end slide lock mechanism can combine a grooved wire with a C-shaped slot cut into a lock plate.

Figure 11:
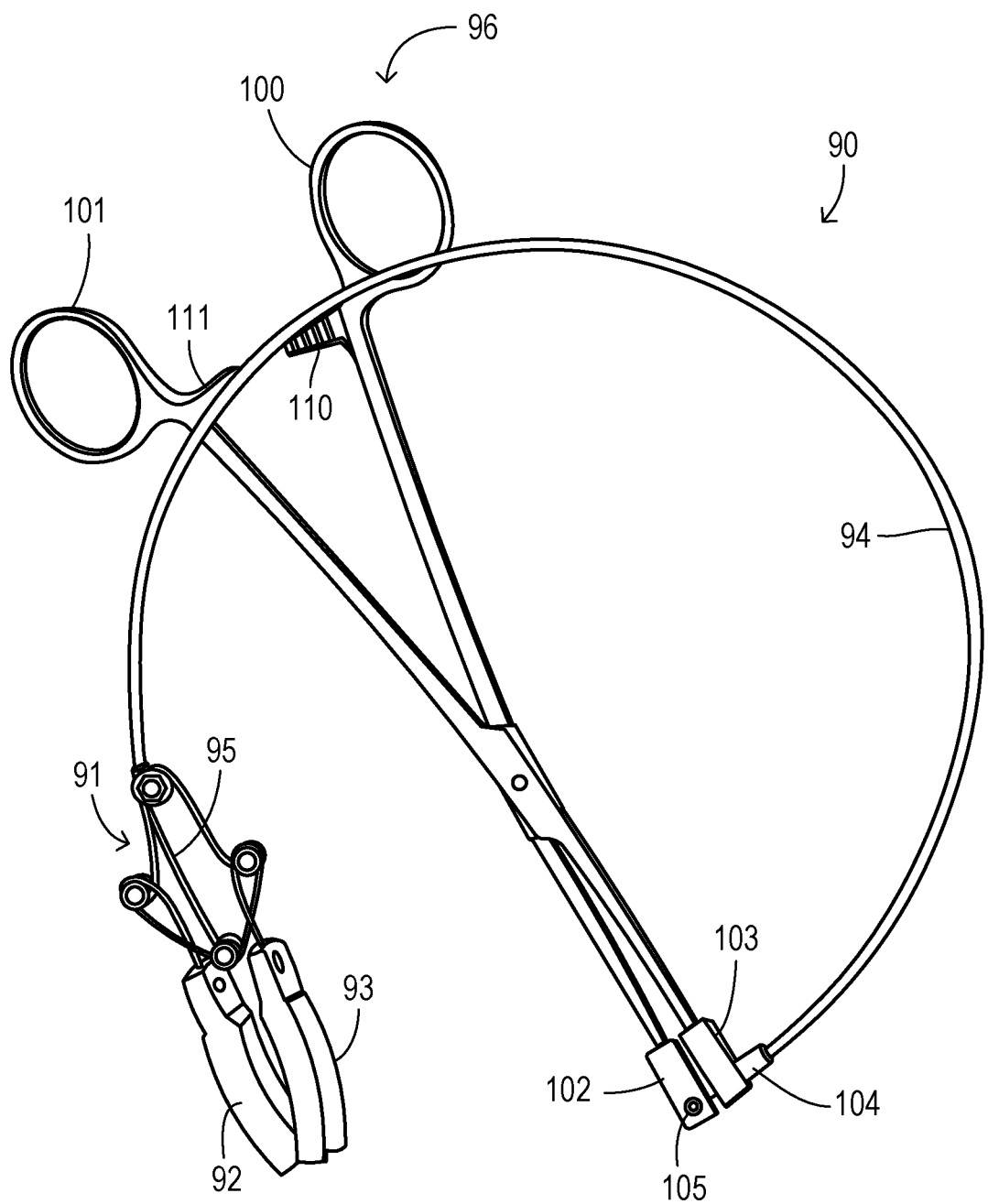
FIG. 11 is a side view of another embodiment of an expander/retractor tool of the invention in a closed configuration.
Figure 12:
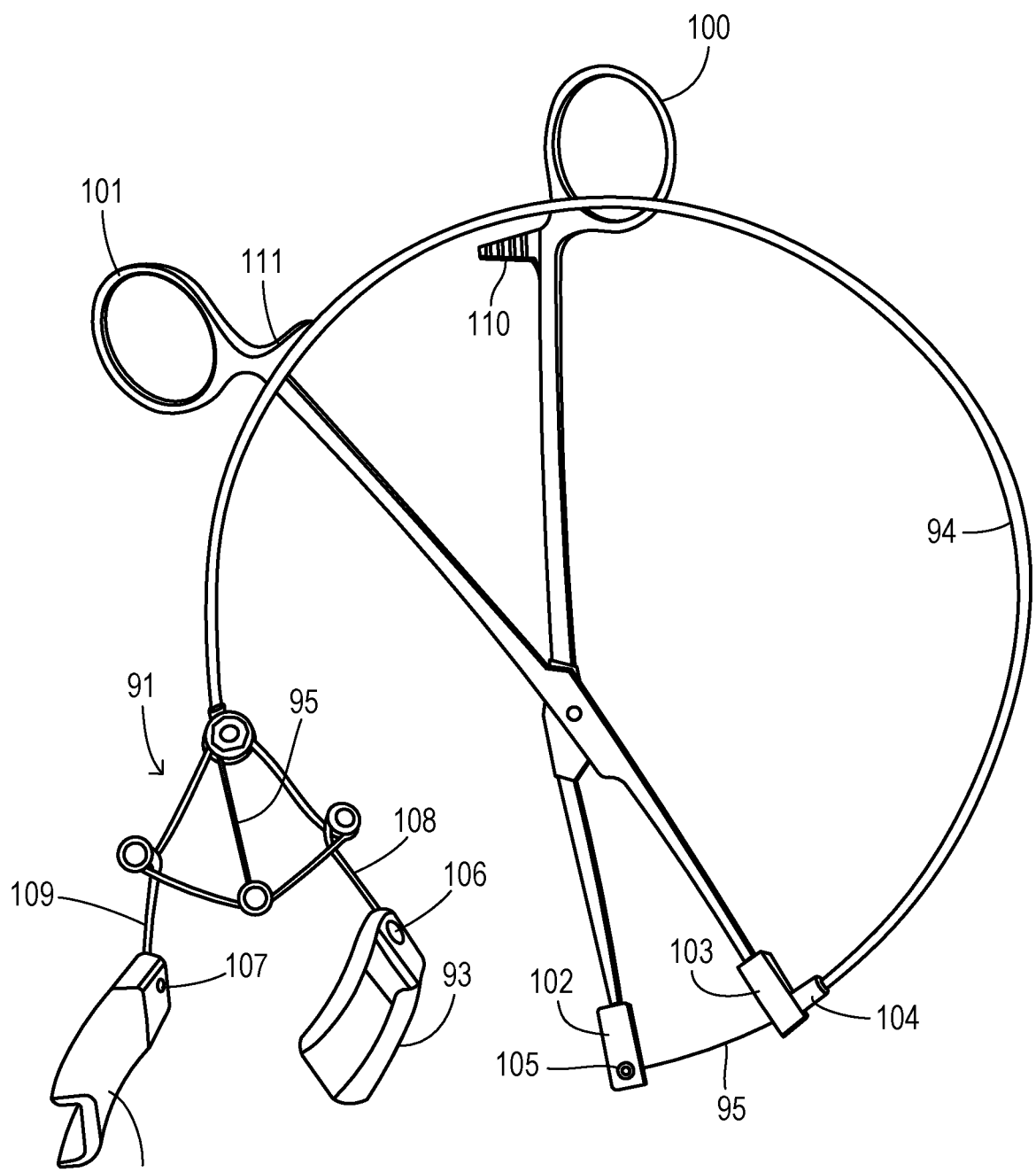
FIG. 12 is a side view of the tool of FIG. 11 in an open configuration.

FIGS. 11 and 12 show a closed state and an open state, respectively, for an alternative embodiment of an expander/retractor tool 90 adapted to enable access through a port (e.g., about 12 mm in diameter) which has a pantograph mechanism 91 controlling retractable blades 92 and 93. Blades 92 and 93 are molded plastic bodies with a curved paddle shape which may be configured to match any desired profile depending upon the tissues to be retracted. By folding retractable blades 92 and 93 to be parallel to the long direction of closed pantograph 91 (i.e., blades 92 and 93 extend along a plane defined by the pantograph pivot points), the tool can be inserted through 12 mm diameter incision hole, resulting in little or no trauma to the patient. A Bowden cable has an outer tube 94 and an inner wire 95. Also, a handle body is replaced with a hinged forceps type of handle which may provide easier adjustment (i.e., control of the deployed width). Hinged forceps members 100 and 101 have finger rings at one end and grasping jaws as the other end. The grasping jaws carry fittings 102 and 103. Fitting 102 has an anchor pin 105 retaining an end of inner wire 95. Fitting 104 has a receiver 104 retaining outer tube 94. By operating the finger rings toward and away from one another, inner wire 95 slides within outer tube 94, causing blades 92 and 93 to close and open. Once blades 92 and 93 are inserted into a working space, they may be rotated at their connection points to become transverse to the plane of pantograph mechanism 95. For example, blades 92 and 93 may include hinges 106 and 107 connected to pantograph 91 allowing blades 92 and 93 to pivot. Alternatively, pantograph wires 108 and 109 may be bendable. A sliding ratchet mechanism 110/111 projecting from forceps members 100 and 101 can be provided to hold the forceps in a secure position.

What is claimed is:

1. An expander/retractor device for minimally invasive cardiac surgery comprising:
    a pantograph mechanism with first and second input pivots and first and second output pivots;
    first and second retraction jaws extending from the first and second output pivots, respectively;
    a compound cable with an outer tube fixed to the first input pivot and an inner wire fixed to the second input pivot; and
    a handle for displacing the inner wire along the outer tube.

2. The device of claim 1 wherein the retraction jaws have adjustable shapes.

3. The device of claim 2 wherein the adjustable shapes of the retraction jaws includes pivoting from within a plane defined by the pantograph mechanism to an orientation transverse to the plane.

4. The device of claim 2 wherein the retraction jaws are comprised of malleable wires bent according to a desired retraction surface shape.

5. The device of claim 4 wherein the malleable wires forming the retraction jaws further form linkages between the input and output pivots of the pantograph mechanism.

6. The device of claim 1 wherein the pantograph mechanism is further comprised of linkages joining the first input pivot to the first and second output pivots and linkages joining the second input pivot to the first and second output pivots.

7. The device of claim 6 wherein the linkages are comprised of malleable wires.

8. The device of claim 6 further comprising output arms coupling the first and second jaws to the output pivots.

9. The device of claim 8 wherein the output arms are comprised of malleable wires.

10. The device of claim 1 wherein the handle is comprised of:
    a body affixed to the outer tube; and
    a plunger slidable within the body and affixed to the inner wire.

11. The device of claim 10 wherein the handle further comprises a lock pin for locking the plunger at a selected position within the body.

12. The device of claim 1 further comprising:
    a locking clip configured to be retained on the first input pivot and to hold the inner wire of the compound cable to lock the pantograph mechanism at a selected position.

13. The device of claim 12 wherein the locking clip is comprised of a C-shaped body with a slot at one end, and wherein the inner wire includes a plurality of beads for bearing against the slot.

14. The device of claim 1 wherein the handle is comprised of:
    a first forceps member with a grasping jaw affixed to the outer tube of the compound cable; and
    a second forceps member hinged with the first forceps member and having a grasping jaw affixed to the inner wire of the compound cable.

* * * * *